United States Patent [19]

Arakawa

[11] Patent Number: 4,682,219
[45] Date of Patent: Jul. 21, 1987

[54] ENDOSCOPE

[75] Inventor: Satoshi Arakawa, Oomiya, Japan

[73] Assignee: Fuji Photo Optical Co., Ltd., Saitama, Japan

[21] Appl. No.: 895,849

[22] Filed: Aug. 12, 1986

[30] Foreign Application Priority Data

Aug. 16, 1985 [JP] Japan .................. 60-125576[U]

[51] Int. Cl.⁴ .................. H04N 7/18; A61B 1/04
[52] U.S. Cl. ............................. 358/98; 128/4
[58] Field of Search .................. 358/98; 128/4, 6

[56] References Cited

U.S. PATENT DOCUMENTS

| | | | |
|---|---|---|---|
| 4,491,865 | 1/1985 | Danna et al. | 358/98 |
| 4,519,391 | 5/1985 | Murakoshi | 128/4 |
| 4,573,450 | 3/1986 | Arakawa | 358/98 |
| 4,622,954 | 11/1986 | Arakawa et al. | 358/98 |

Primary Examiner—Howard W. Britton
Assistant Examiner—John K. Peng
Attorney, Agent, or Firm—Parkhurst & Oliff

[57] ABSTRACT

An endoscope includes in the viewing head of its insertable section into a cavity of a living body an image sensor for generating a video signal which in turn is transmitted to a television display to be visualized thereon as a television picture. The image sensor with a shape such as a plate is located in a plane containing the longitudinal center line of the viewing head. In the present endoscope, a prism to be cemented to the image sensor is shielded in the periphery thereof by a light shielding material except for an image pick-up light path which is so positioned as to face the image area of the image sensor, whereby any lights other than a light contributing to forming an image are prevented from entering the image sensor.

6 Claims, 6 Drawing Figures

ENDOSCOPE

BACKGROUND OF THE INVENTION

1. Field of the Invention

The present invention relates to an endoscope and, more particularly, to an endoscope which has as an image pick-up device a plate-like image sensor disposed within a viewing head thereof and is capable of outputting an optical image obtained by an objective lens assembly in the form of a video electric signal.

2. Description of the Prior Art

In addition to endoscope of a type having an optical fiber bundle as its image guide means, conventionally there have been proposed TV endoscopes of a type employing as an image pick-up device a plate-like image sensor formed by a combination of charge transfer elements, such as a charge coupled device (CCD) comprising a great number of small photosensitive picture elements (pixels) arranged in matrix. Such TV endoscopes are found advantageous over the above-mentioned conventional endoscopes employing the optical fiber bundle as the image guide means thereof in that they have a longer durability, they are capable of processing an electric signal as a video image output in various ways, and they can be produced at lower costs. Therefore, the practical application of the TV endoscopes is now under consideration.

Now, the TV endoscope is requested to satisfy two requirements; one requirement is to reduce the outside diameter of the endoscope to the degree that it can be inserted into a cavity of a living body; and, the other is to improve the resolving power of the image sensor, that is, to increase the number of picture elements on the image sensor. Thus, it becomes a very important point how to construct the forward end portion of the endoscope, especially how the image sensor of an objective lens assembly permitting the image sensor to form an optical image is arranged efficiently in space.

Accordingly, in order to arrange a plate-like image sensor without enlarging the forward end portion of the endoscope, the present applicant has already proposed an arrangement in which the plate-like image sensor is provided in a plane including the center axis of the endoscope in the longitudinal direction thereof, an objective lens assembly is disposed on one side of the plate-like image sensor with the axial line thereof being parallel to the axial line of the plate like image sensor, a right-angled prism is provided in the rear of the objective lens assembly to turn a light path at 90°, and a light emitting surface is cemented to the image sensor (Japanese Patent Publication No. 104915 of 1985). This arrangement permits the effective use of the outer diameter of the endoscope, making it possible to provide a wide image sensor in the endoscope forward end portion of limited diameter.

By the way, to observe an affected part through an objective lens assembly, it is necessary to irradiate the affected part by use of light guides. Therefore, the light guides each formed of an optical fiber bundle or the like are provided on opposite sides of the objective lens assembly in parallel thereto in the forward end portion of the endoscope. In other words, the light guides are disposed close to the light receiving surface of the image sensor. The optical fiber bundle forming the light guide is covered with a tube of silicone rubber or the like and is inserted into the endoscope. However, since the forward end portion of the optical fiber bundle must be fitted into the opening of a metal barrel, the tube is peeled off from the forward end portion of the optical fiber bundle or the light guide, providing an exposed portion in the light guide which is not covered with the tube. Thus, in the prior art, such exposed portion of the light guide is hardened by means of epoxy resin or the like to prevent it from getting loose. As a result of this, there is a possibility that the light of the light guide may leak from the exposed portion to the light receiving surface of the image sensor. If any light other than the light from the objective lens assembly enters an image area forming the image pick-up area of the image sensor, then the image pick-up function of the image sensor is impeded. Also, if any light other than the light contributing to the image formation enters a storage area serving as an image transfer area, then the transfer function of the image sensor is impaired. Consequently, inaccurate images may be obtained or images obtained may be blurred due to blooming or the like.

To eliminate the above-described disadvantages, the applicant has proposed an endoscope in Japanese Utility Model Application No. 130217 of 1984 in which a light shielding plate or a mask is interposed between an image sensor and an objective lens assembly and is formed with a round hole in the portion thereof where a light from a prism in the objective lens assembly enters, whereby lights are prevented from entering from light guides and thereby only the optical images that are obtained from the objective lens assembly can be received by the image sensor.

It is true that the endoscope disclosed in the above-mentioned application is found satisfactory in eliminating the drawbacks found in the before-described prior art endoscopes. But, in the above endoscope, when the light shielding plate is cemented to the image sensor, if the center of the round hole of the light shielding plate is set out of alignment with the center of the image area of the image sensor, then an observed image is projected on a monitor television off from the center thereof. For this reason, the light shield plate must be accurately aligned with the image area. Also, if the center of the round hole of the light shielding plate is set out of the center of the prism in the objective lens assembly, the optical image from the objective lens assembly is then shielded in part by the light shield plate and thus the observed image is projected on the monitor TV in a manner that it is partially cut away. Therefore, it is not easy to assemble the endoscope including the accurate alignment of the objective lens assembly, light shield plate and image sensor. Further, the objective lens assembly and the image sensor are cemented to each other by means of a transparent adhesive resin. However, the transparent adhesive resin may produce air bubbles which give rise to the diffused reflection of a light incident from the prism.

SUMMARY OF THE INVENTION

The present invention aims at eliminating the disadvantages found in the above-mentioned endoscope proposed by the applicant in the above-mentioned application.

Accordingly, it is an object of the invention to provide an improved endoscope in which an image sensor, lenses in an objective lens assembly and the like disposed in the forward end portion of the endoscope can be assembled with ease and also any lights other than a light contributing to forming an image are prevented from entering the image sensor so as to be able to obtain an accurate and clear video image.

In accomplishing the above object, according to the invention, in an endoscope provided with a plate-shaped image sensor in the forward end portion thereof and capable of outputting as a video signal an optical image obtained by an objective lens assembly, the endoscope is characterized in that, among optical elements forming the objective lens assembly, an optical element to be cemented to the image sensor is shielded from light with a light shielding material in the periphery thereof except for an image pick-up light path formed therein, and that, with the center of the image pick-up light path in the optical element being aligned with the center of the image sensor, the objective lens assembly and the image sensor are cemented to each other.

BRIEF DESCRIPTION OF THE DRAWINGS

The exact nature of this invention, as well as other objects and advantages thereof, will be readily apparent from consideration of the following specification relating to the accompanying drawings, in which like reference characters designate the same or similar parts throughout the figures thereof and wherein.

DETAILED DESCRIPTION OF THE PREFERRED EMBODIMENTS OF THE INVENTION

Detailed description will hereunder be given of the preferred embodiments of an endoscope according to the present invention with reference to the accompanying drawings.

Figure 1:
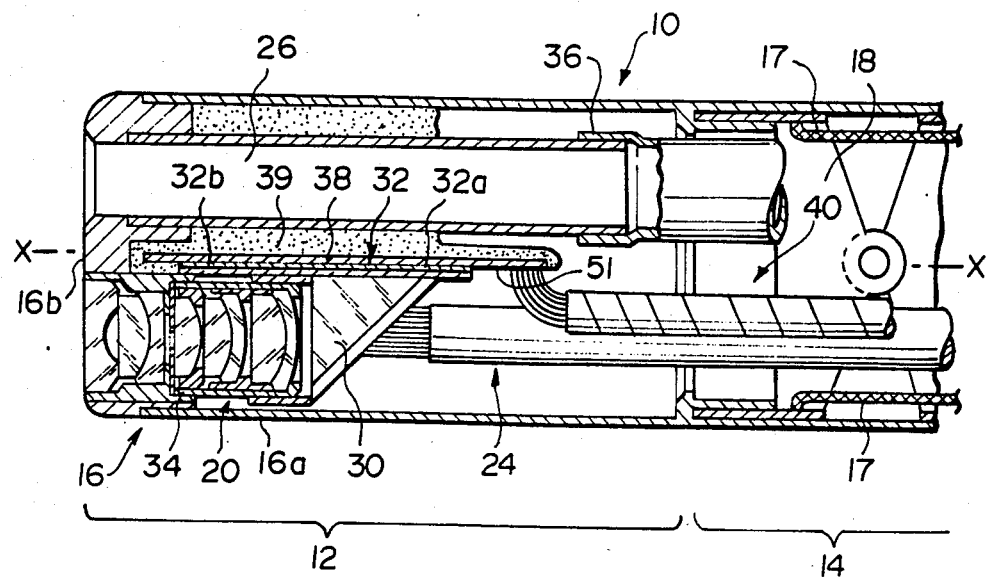
FIG. 1 is a side sectional view of a first embodiment of the invention which is applied as a direct vision type endoscope.
Figure 2:
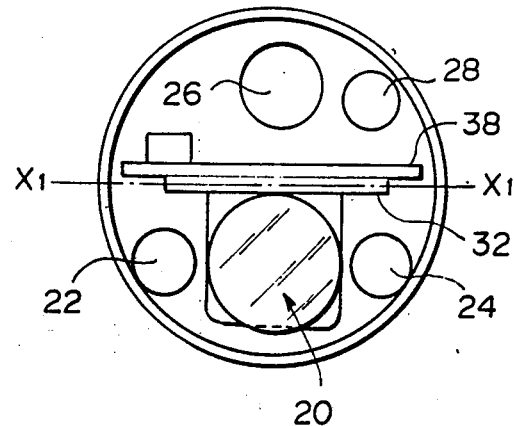
FIG. 2 is a schematic elevational view of the above embodiment shown in FIG. 1.

Referring first to FIGS. 1 and 2, they are respectively a side sectional view and a schematic elevational view of a forward end portion of a first embodiment of the present invention which is applied as a direct vision type of endoscope. As shown in FIG. 1, the forward end portion of the endoscope insertion section, designated by 10, comprises a rigid part or a viewing head 12 and a bendable part 14. The viewing head 12, which is composed of a metal barrel 16, is rigid or inflexible. This metal barrel 16 comprises a tubular metal 16a forming a main portion of the viewing head 12 and a disc-shaped metal 16b fitted into the front end of the tubular metal 16a. The bendable part 14 is formed of a plurality of articulated rings 18 interconnected with one another, and is free to flex vertically and laterally by means of operation of operation wires 17. As shown in FIG. 2, within the endoscope forward end portion 10, there are inserted an objective lens assembly 20 as well as two light guides 22, 24 on opposite sides thereof, a forceps channel 26 thereabove, and an air and water supply channel 28 right thereabove, respectively extending in the longitudinal direction (that is, in the horizontal direction in FIG. 1) of the endoscope. As can be seen clearly from FIG. 1, the objective lens assembly 20, generally having a plurality of lenses, is provided in the rear thereof with a right-angled prism 30 adapted to turn the optical path of the objective lens assembly at a right angle and having a light emitting surface to which a rectangular and plate-like image sensor 32 is cemented. The image sensor 32 is located close to and along a plane containing the longitudinal central axis (that is, a line shown by line X—X in FIG. 1 and XI—XI in FIG. 2) of the endoscope, permitting effective use of the outside diameter of the endoscope. The optical parts forming the objective lens assembly 20 are respectively fixed to the metal barrel 16 directly or via a mirror frame 34 or the like. The disc-shaped metal 16b is formed with a plurality of openings which correspond to the above-mentioned various channels respectively. For example, as shown in FIG. 1, a forceps tube 36 is connected to the forceps channel 26, so that a forceps can be inserted through the forceps channel 26 or the opening corresponding thereto.

Figure 3:
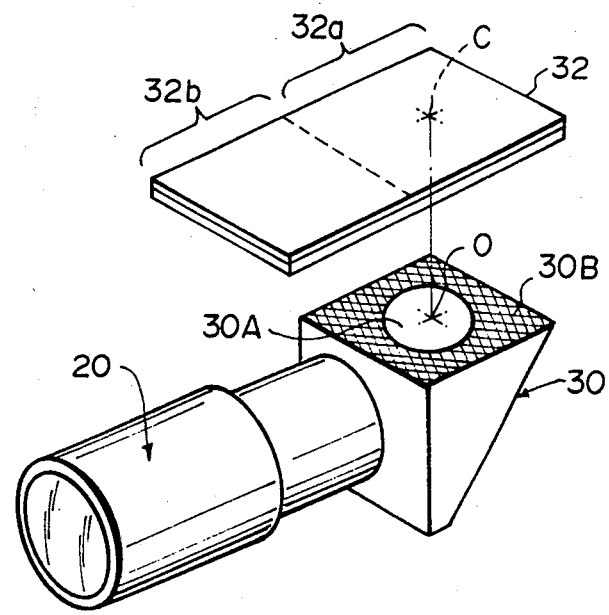
FIG. 3 is an exploded perspective view of the main portions of the above first embodiment shown in FIGS. 1 and 2.

Referring now to FIG. 3, there is shown an exploded perspective view of the cemented portion between the objective lens assembly 20 and the image sensor 32.

The image sensor 32 comprises an image area 32a for picking up an image from a light received from the prism 30, and a storage area 32b for transferring the image received by the image area 32a. The image sensor 32 also includes a seating plate 38 which is formed in the rear portion thereof with a connector section 51 for connecting lead wires 40 thereto. The lead wires 40 are used to transmit a driving signal from a drive circuit in a control unit, not shown, to the image sensor 32 and also to send a video signal from the image sensor 32 to the control unit.

As shown in FIG. 3, the surface of the prism 30 to be cemented to the image sensor 32 is chrome plated or covered with a light shielding paint except for a round hole 30A formed therein, providing a light shielding portion 30B. In assembly, the center O of the round hole 30A of the prism 30 must be aligned with the center C of the image area 32a of the image sensor 32 before the prism 30 is cemented to the image sensor 32. Thanks to this, only an optical image obtainable through the round hole 30A of the prism 30 from the objective lens assembly 20 is allowed to enter the image pick-up surface of the image area 32a. That is, any lights other than the optical image passing through the round hole 30A are shielded by the light shielding portion 30B of the prism 30 and thus are prevented from entering the image pick-up surface of the image area 32a of the image sensor 32. The portions of the image sensor 32 located adjacent to the periphery of the prism 30, after they are cemented to each other, are also covered with a light shielding paint so that no other lights than the above-mentioned optical image are permitted to enter the image pick-up surface of the image area 32a of the image sensor 32.

Also, as shown in FIG. 1, between the seating plate 38 of the image sensor 32 and the metal barrel 16 there is interposed a heat conductive material 39 which can be obtained, for example, by mixing epoxy resin with metal powder such as aluminium powder. The heat conductive material 39 is in FIG. 1 filled up in a space formed upwardly of the seating plate 38 of the image sensor 32.

As has been described hereinbefore, according to the endoscope of the invention, the surface of the prism 30 to be engaged with the image sensor 32 is treated to provide the light shield portion 30B except for the round hole 30A, so that only the optical image obtained from the objective lens assembly 20 through the round hole 30A is allowed to enter the image sensor 32, that is, any lights other than the above-mentioned optical image, especially, lights from the light guides 22, 24 disposed to the prism 30 are prevented from entering. Also, it is easy to assemble by cementing the prism 30 and the image sensor 32 simply by aligning the center O of the round hole 30A of the prism 30 with the center C of the image area 32a of the image sensor 32. In other words, the invention provides an endoscope which is capable of projecting an observed image on a monitor TV in the form of an accurate video image.

Figure 4:
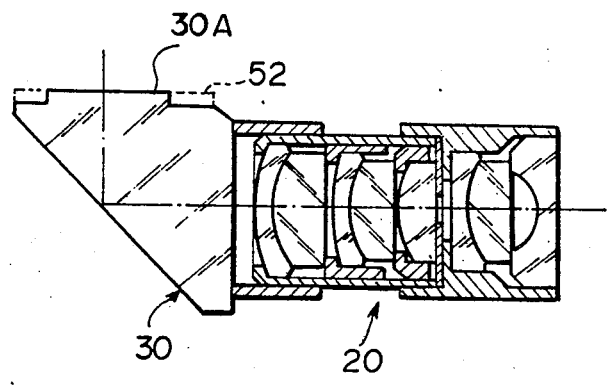
FIG. 4 is a side view of another embodiment of a prism employed in the above first embodiment as an element of an objective assembly.

In the above-mentioned embodiment, a chrome plating is treated on the prism 30 to provide the light shield portion 30B, but the invention is not limited to this and any other materials capable of shielding lights may be used. Also, as shown in FIG. 4, a portion of the upper surface of the prism 30 may be formed with a step or raised higher above the remaining portion of the prism upper surface to provide a projected, round surface 30A, and a light shielding coating 52 may be formed in the portions of the prism upper surface other than the projected round surface 30A. For this purpose, a light shielding material is not limited to the light shielding coating 52, but a light shieldable thin resin plate may also be used.

Figure 5:
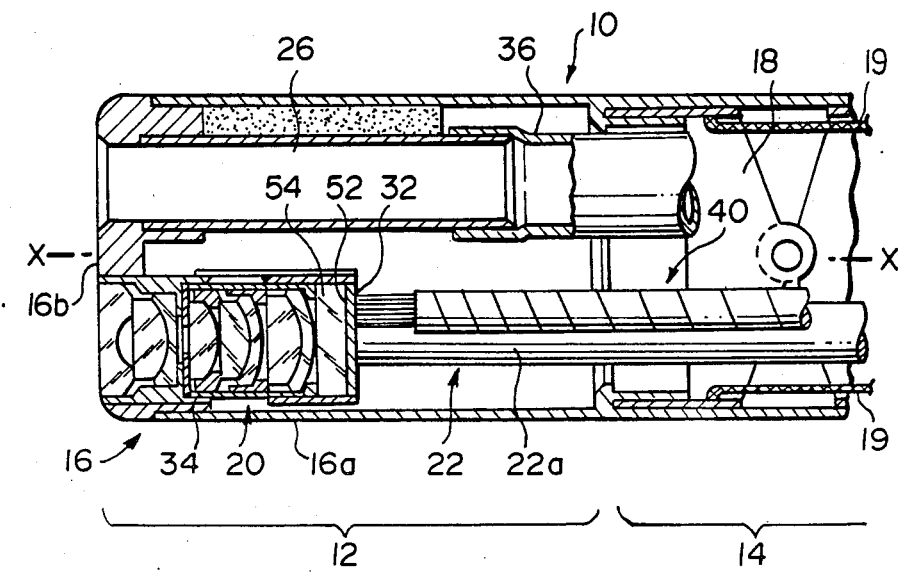
FIG. 5 is a side sectional view of a second embodiment of the invention.
Figure 6:
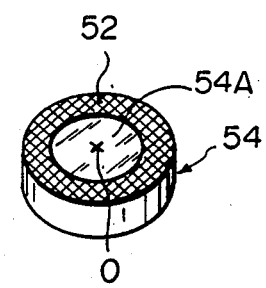
FIG. 6 is a perspective view of a lens of the objective lens assembly employed in the invention.

Referring next to FIG. 5, there is shown a sectional view of a second embodiment of the invention. As shown in FIG. 5, an image sensor 32 is formed of a highly sensitive CCD or the like and is disposed in a direction perpendicular to the central axis X—X of the endoscope forward end portion. A lens 54 forming an objective lens assembly 20 is directly cemented to the image sensor 32. As shown in FIG. 6, the lens 54 is chrome plated in a ring form, except for a round hole 54A formed therein. With the image sensor 32 constructed in this manner, as in the previously described first embodiment, any lights from unnecessary portions other than a preselected image pick-up system are prevented from entering, and it is easy to assemble the lens 54 and the image sensor 32 simply by aligning the center O of a central circle 54A of the lens 54 with the center C of the image area of the image sensor 32.

As has been described hereinbefore, according to the invention, since a light shielding member is included in the optical elements of an objective lens assembly to thereby cover all portions except for an image pick-up light path, the center of the objective lens assembly can be easily aligned with the center of the image sensor and thus it is easy to assemble an endoscope which is capable of projecting an accurate observed image on a monitor TV.

It should understood, however, that there is no intention to limit the invention to the specific forms disclosed, but on the contrary, the invention is to cover all modifications, alternate constructions and equivalents falling within the spirit and scope of the invention as expressed in the claims.

What is claimed is:

1. An endoscope for displaying an object of interest on a screen of a television set in response to a video signal obtained from a plate-shaped image sensor provided in the forward end portion of an insertable flexible section of said endoscope, said endoscope comprising:
    said plate-shaped image sensor provided in a plane including the longitudinal center axis of said insertable flexible section of said endoscope; and,
    an objective lens assembly including a light entering surface and a light emitting surface to be cemented to said image sensor, said light emitting surface being shielded in the periphery thereof by a light shielding material except for an image pick-up light path.

2. An endoscope as set forth in claim 1, wherein said objective lens assembly is located in one of space portions of said insertable flexible section of said endoscope.

3. An endoscope as set forth in claim 2, wherein said objective lens assembly includes a prism having a light emitting surface, said light emitting surface being cemented to said image sensor.

4. An endoscope as set forth in claim 3, wherein said light emitting surface of said prism is shielded in the periphery thereof by a light shielding material except for an image pick-up light path.

5. An endoscope as set forth in claim 4, wherein said light emitting surface of said prism is formed therein with a round, projected surface which corresponds to said image pick-up light path, and wherein the other portions of said prism light emitting surface than said round, projected surface thereof are covered with a light shielding coating film.

6. An endoscope as set forth in claim 4, wherein said light shielding material comprises chrome plating or a light shielding paint.

* * * * *